United States Patent [19]

Maurer

[11] Patent Number: 5,534,249
[45] Date of Patent: Jul. 9, 1996

[54] METHOD OF REDUCING MALODOR USING METAL COMPLEX

[75] Inventor: Gerald L. Maurer, Cincinnati, Ohio

[73] Assignee: National Research Labs, Cincinnati, Ohio

[21] Appl. No.: 440,828

[22] Filed: May 15, 1995

[51] Int. Cl.$^6$ .......................................... A61L 9/01
[52] U.S. Cl. ................. 424/76.3; 424/76.1; 424/76.71; 424/76.5
[58] Field of Search ................... 424/76.5, 76.1, 424/76.21, 76.3, 76.5

[56] References Cited

U.S. PATENT DOCUMENTS

| | | | |
|---|---|---|---|
| 4,180,473 | 12/1979 | Maurer et al. | 424/DIG. 6 |
| 4,278,610 | 7/1981 | Maurer et al. | 556/114 |
| 4,708,864 | 11/1987 | Maurer | 424/405 |

*Primary Examiner*—Thurman K. Page
*Assistant Examiner*—S. Howard
*Attorney, Agent, or Firm*—Dinsmore & Shohl

[57] ABSTRACT

A method of reducing malodor in the environment by using a (1:1) dialkali monometal polyfunctional organic ligand chelate is disclosed. The 1:1 metal complex functions as an oxidation catalyst in the presence of oxygen to neutralize odor causing materials. The odor is chemically neutralized by the 1:1 metal complex, not just masked by a stronger scent.

13 Claims, No Drawings

METHOD OF REDUCING MALODOR USING METAL COMPLEX

FIELD OF INVENTION

This invention relates generally to a compound for use in the reduction of malodor in the environment. More specifically, this invention relates to the use of a (1:1) metal complex consisting of dialkali monometal polyfunctional organic ligand chelate functioning as an oxidation catalyst in the presence of oxygen to oxidize odor causing materials, thus eliminating malodor. The metal complex can be delivered in a vapor, liquid, or solid phase and can be added to vapor, gas, liquid, or solid odorous materials. This invention also relates to a process for the chemical neutralization of odor causing chemicals.

BACKGROUND OF INVENTION

Odor causing materials originate from a variety of sources in the environment. Odor materials must be capable of travelling through the air to activate the olfactory senses. However, the materials themselves may be solid, liquid, or gaseous. Odorous materials can originate from both organic and inorganic sources. Some examples of common odor causing materials in the environment are urine, feces, food waste, and bilge water.

Most odor causing materials generally contain similar or common types of odor causing molecules, such as, for example, skatoles, indoles, dimethyldisulfide, amines, and ammonia. Nature eliminates odors caused by these and other chemicals by slowly combining the materials that create odors with oxygen from the air. This process is called oxidation. The metal complexes of the present invention achieve the same results at a greatly increased rate of speed, within minutes or even seconds. One especially successful metal complex in the 1:1 dialkali monometal polyfunctional organic ligand chelate family is disodium monocopper (II) citrate dihydrate, CAS Registry #65330-59-8. This material is sold under the trademark NoRoma MCC® by Bio Systems Inc. of Cincinnati, Ohio.

One application for the metal complexes of this invention is in controlling odors in portable toilets and toilets used in the transportation industry, e.g. locomotives, passenger cars, airplanes, etc. There has been interest in these compounds for use by coroners, morgues, and funeral homes. This material may also be used to eliminate human scent which could be a boon during activities such as hunting. These metal complexes work especially well in neutralizing odors caused by sulfurous compounds and other nitrogen containing substances such as ammonia and skatoles, as well as hydrogen sulfide. It is seen that these metal complexes have a wide variety of industrial applications, as well as environmentally beneficial uses.

Another industrial application would be in removing ammonia odors. Ammonia is used in refrigeration coils and commercial freezers and tends to leak into the environment. Air, concentrated with ammonia gas is unsuitable for supporting life and this contaminated air can be cleared by atomizing an appropriate mixture containing monocopper citrate into the contaminated air the form of a fine dispersion of droplets. This particular application is remarkable in that the operation typically occurs in an environment where the temperature is below −20° F. Therefore, it is seen that the metal complexes of this invention are useful under a whole host of environmental conditions.

U.S. Pat. No. 4,278,610 to Maurer, et al. (the '610 patent), discloses a method of making an organic metal salt or complex. The generic chemical compound is described in this patent as is the chemical reaction used to make it. The entire disclosure of the '610 patent is incorporated herein by reference.

U.S. Pat. No. 4,180,473 to Maurer, et al. (the '473 patent), discloses a method of transporting metal ions introducing a metal complex into a medium containing a moiety which medium has an affinity for the metal ion. The complex releases the ion in a controlled manner upon demand by the medium. The '473 patent uses disodium monocopper citrate, or MCC, as an example of chemical that can be used to deliver metal ions, in this case copper, to a system that requires the metal ion. The '473 patent describes a variety of situations where the metal ion is either desirable or necessary. Metal machining operations and control of microbiological activities are among some of the examples of systems that need or benefit from the copper ion distributed from a metal complex such as MCC. The odor controlling characteristics of MCC are not discussed nor are they suggested in either the '473 or '610 patents. Also there is no discussion of these characteristics in any other known literature. The entire disclosure of the '473 patent is incorporated herein by reference.

SUMMARY OF THE INVENTION

While not an exhaustive list, the following describes some of the important features and objectives of the present invention.

One objective of this invention is to provide a method of reducing malodor in the environment by delivering an effective amount of a metal complex comprising dialkali monometal (1:1) polyfunctional organic ligand chelate. This metal complex functions as an organic catalyst in the presence of oxygen to oxidize the odor causing material thereby eliminating the offensive odor.

It is a further objective of this invention to remove odor more rapidly than natural forms of oxidation, by oxidizing the odor causing chemicals more rapidly than natural forms of oxidation. Thus, the metal complexes of this invention act as an oxidation catalyst. This catalytic oxidation works at a much faster rate than natural oxidation.

The catalytic metal complex molecules do not themselves combine with common odor causing molecules or the oxygen, however, they must come in contact with the odor causing molecules to catalyze the neutralization reaction. Therefore, thorough mixing of the MCC product with the odor causing material is essential. Once the reaction is complete, the metal catalyst is freed, and it returns to its complexed state. It is then ready to repeat the reaction on other odor causing molecules. This explains why such a small amount of product can be effective in very large volumes of odor causing material.

Another object of this invention is to provide metal complexes for removing malodors, for use in combination with other chemicals, e.g. cleaning products, certain biocides, sanitizers, etc., without sacrificing the effectiveness of the catalytic metal complex or decreasing the effectiveness of the other chemicals. As would be expected, there are certain chemicals which the metal complexes are not compatible with such as, strong acids, strong alkalis and some chelating agents (e.g. EDTA, DPTA, NTA, aluminum, and primary amines). Although these chemicals are rarely found in cleaning products, biocides or sanitizers, small portions may be found in bilge or sewage solutions. Therefore, in a solution that contains small amounts of chemicals that might destroy the chemical quantities of the metal complex, an excess, over that which is necessary to control odor, may have to be added. This is generally not a problem, because as discussed above, usually, very small amounts of the metal complexes are required. Therefore, only small excess amounts are required. Also, buffering adjuncts may be added to the metal complex to regulate the pH of the odor causing material, thus making the metal complex more efficient.

Prior art compositions for "odor control" rely heavily upon "odor-masking," rather than actually controlling or modifying the odor causing chemical. The compositions of this invention are designed to react chemically with the odor-causing agent at its source, thereby eliminating the cause of the odor rather than simply masking the effects of the odor. Typical odor masking utilizes strong, often overbearing and even unpleasant perfumes or "masking agents." "Masking agents" are generally perfumes that simply, in a very temporary fashion, distract the olfactory sense from one unpleasant odor by means of a second, less offensive odor. When prior art compositions are used, the sense of smell is affected; with the present invention, the actual causes of odors are neutralized.

In accordance with one aspect of the present invention, there is provided a method of reducing malodor comprising the steps of: delivering at or near the source of said malodor an effective amount of a metal complex comprising 1:1 dialkali monometal polyfunctional organic ligand chelate, said metal complex acting as an oxidation catalyst in the presence of oxygen to chemically neutralize the source of said malodor.

DETAILED DESCRIPTION OF INVENTION

The following detailed description is with reference to the employment of the metal complexes of the present invention in removing malodors from various environments.

It is well-known that the 1:1 complexes of metals with polyfunctional organic ligands can serve to deliver active metallic ions in an aqueous medium and result in the reaction of the ion with a substance demanding the ion. See U.S. Pat. No. 4,180,473. It is also well-known that the insertion of Lewis acids into the aqueous solution of the 1:1 complexes results in the destruction of the complex with the formation of a metal derivative and a free, substituted polyfunctional organic ligand, e.g.:

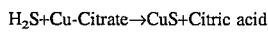

$H_2S + Cu\text{-Citrate} \rightarrow CuS + \text{Citric acid}$

This reaction mechanism neutralizes the hydrogen sulfide and its attendant odor, and is stoichiometric. A similar mechanism operates when, for instance, ammonia is added to an aqueous solution of the metal complex, again, with a neutralization of the odor-causing properties of the ammonia. Based on this basic reaction mechanism, highly useful, unique compositions have been formulated so as to optimize and enable this mechanism to function in odor control compositions.

However, the metal complexes of this invention surprisingly can also chemically neutralize odor causing chemicals by themselves (i.e. without Lewis acids), in a non-stoichiometric, catalytic fashion, e.g.:

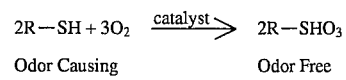

$$2R\text{--}SH + 3O_2 \xrightarrow{\text{catalyst}} 2R\text{--}SHO_3$$

Odor Causing          Odor Free

Therefore, the simplest way to practice this invention is to provide an effective amount of the metal complex at or near the source of the odor. The metal ion then dissociates and becomes available to catalyze the neutralization reaction. After the odor causing chemical has been neutralized by catalytic oxidation, the metal ion reassociates with the organic ligand and is then ready to catalyze another neutralization reaction. The 1:1 metal complexes associate and disassociate rapidly, further enhancing their ability to be effective catalysts. Although copper and zinc are discussed in the preferred embodiments, manganese and other metals also exhibit odor controlling properties.

There are circumstances where the odor causing chemicals may be in an environment which is not compatible with the metal complexes of this invention. As stated above, in order to neutralize an odor-causing substance, the dissociated metal ion must come into physical contact with the odor-causing chemicals. Furthermore, when the metal complex is introduced into a complex mixture there may be competition for the metal ion catalyst between odor-causing chemicals and other non-odorous chemicals. Therefore, the metal complex may be bound by the interfering substance, thereby diminishing the deodorizing characteristics of the metal complex.

Furthermore, in many instances, the long term prevention of odors cannot be accomplished simply by adding a solution of the 1:1 metal complex to the odor-causing substance. Sometimes, the odor neutralizing power of the metal must be gradually released so that it becomes available for odor neutralizing activities over an extended time frame.

As stated above, it has been found that odor-causing agents can be present in a great diversity of environments: solid; semi-solid; high, neutral and low pH; and high or low temperatures. Combinations of these variables present special difficulties and demand specialized mixture of the 1:1 metal complexes with adjuncts and/or carriers, to enable the odor control function to operate satisfactorily. For instance, the largest user of odor control agents is the general consumer, such products being needed in essentially every home and business, from time to time. Therefore these products have been carefully designed to assure convenience, long-term storage capability and ease of use together with safety. A simple, aqueous solution of the 1:1 metallic complex may not meet these requirements. For example, a product must often resist freezing which would require the addition of adjuncts to lower the freezing point of the metal complex and its carrier. Another embodiment may include an adjunct to control in some fashion the inherent corrosivity of the metallic complexes, with reference to, for instance, aerosol spray containers made of both ferrous and nonferrous metals.

By accommodating these requirements for storage and use, it has been found that the efficacy of the odor control mechanism can be hindered severely or even eliminated by the additional ingredients. Such ingredients must therefore be carefully chosen in order to avoid loss of odor control capabilities.

The following are preferred embodiments of the present invention that satisfy specific requirements presented by the use environment and/or the odor source. It will be seen that particular requirements must be met for some of the formulations, in order to accommodate the operational parameters of the finished product. These examples are not exhaustive, but rather they are disclosed for illustration purposes only.

EXAMPLE 1

Neutralization of Ammonia Gas

Ammonia gas is utilized as a refrigerant in food-storage freezer facilities. Leakage of ammonia gas into the environment of the freezer or "cold room" is a common occurrence. Special protective equipment must be donned by repair crews so as to effect necessary repairs in the hostile environment of both extreme cold (often reaching 20 to 30 degrees below zero Fahrenheit) and high toxicity due to the ammonia gas, which cannot be inhaled by humans in more than trace quantities without dire, adverse physiological reactions. Once repairs of the equipment which caused the leaks have been completed, the entire confines of the refrigerated area would normally have to be to be totally evacuated in order to remove ammonia gas from the environment. This procedure necessitated, in most cases, the risk of raising the temperature of the frozen products above a safe level because of the loss of chilled air. Also, no "perfume" (prior art deodorizer), could be tolerated, lest the stored products be contaminated.

An odor-free product which may be atomized or sprayed into the ammonia-containing environment, which would remain liquid even at temperatures well below the freezing point of water, and which would be non-toxic should it come in contact with materials stored in the freezer compartment such as foodstuffs, product would obviate the need for evacuation of the cold room. A composition which satisfies all of the above requirements is disclosed below, all percentages being in weight percent:

| Propylene Glycol, U.S.P. grade | 50% |
| --- | --- |
| Triton X-100 | 5% |
| Disodium monocopper(1:1)citrate | 5% |
| Water | 30% |
| Triethanolamine, U.S.P. | 10% |

This composition functions well in the sub-freezing environment described above. Surprisingly, it was found that the 1:1 complex functioned optimally at a slightly elevated pH (engendered by the triethanolamine), of approximately 9.5. The Triton compound, a potent surfactant, permitted the formation of extremely tiny droplets of spray which were very efficient in contacting the ammonia gas, with subsequent neutralization. The propylene glycol acted as a safe, but effective, antifreeze agent. Approximately one U.S. pint (approximately 480 milliliters) of this composition, delivered as a spray, reduced the ammonia vapors present to undetectable levels in an area comprising approximately 8,000 cubic feet of refrigerated space.

EXAMPLE 2

Deodorizing Carpet

Carpeting, both domestic and commercial, is often subject to heavy traffic and abuse. In eating establishments, for example, both patrons and employees use and abuse carpeting by spilling foodstuffs which become embedded in the fibers of the carpeting. It has been found that these materials oftentimes find their way into the carpet padding and even into the flooring material under the carpeting. General cleaning of spillage areas has been found lacking in its ability to remove residual odors generated as fatty materials and proteinaceous compounds are decomposed by bacterial and inherent chemical activities such as the tendency of butterfat, for instance, to hydrolyze with the release of the highly odoriferous butyric acid. It is impossible to effectively eliminate such odors by simply using masking agents, as found in the prior art. Strong chemical reagents such as oxidizing compounds found in bleaches destroy the integrity of the carpeting. Their use destroys the flooring as well as the odor. Foul odors in restaurants or in home carpeting are highly objectionable from an aesthetic standpoint and require safe, nondestructive and efficient elimination.

A desirable product to remove carpet odors would be one which can be applied to the surface of a carpet and which would penetrate through the carpeting to the odor source, where chemical reaction would eliminate the odor source. The product must not have any odor of its own, so as not to be detectable by persons in the immediate vicinity of use. The product should be colorless, if possible, so as not to "stain" or otherwise discolor the carpeting. It must be non-toxic so as not to contaminate the environment with potentially dangerous chemical substances.

Two compositions were prepared to meet these requirements:

Composition A: Powdered Carpet Deodorizer

| Microencapsulated disodium monocopper(II)citrate (MCC) | 1% by weight |
| --- | --- |
| Sodium bicarbonate | 99% |

This product is "sprinkled" over the area of spillage after having cleaned the area in a conventional manner, i.e. soap and water. The carpeting is permitted to dry before application of this composition. Because of the finely divided nature of this unique composition, it readily infiltrates between the fibers of the carpet and underpad, becoming entangled at the origins of these fibers. This dispersion of the dry powder can be aided by gentle, manual or mechanical agitation of the carpet surface. The result is that the powder composition literally "disappears" into the fabric of the carpet.

Following this initial application of the powder composition, water is sprayed onto the soiled area. The water dissolves the sodium bicarbonate which acts as a buffer at approximately pH 5.2; this buffer solution releases the MCC from the microcapsulates, resulting in a buffered solution of MCC in intimate contact with the odor-causing agents in and below the carpet pile. Because this solution is below the surface of the carpet, there is no color visible, although the solution itself is blue. The odor is then completely neutralized.

An even more preferred embodiment of Composition A is to microencapsulate the MCC in a cellulose acetate microsphere. The microencapsulated particles resist atmospheric moisture and even surface moisture; and, they readily yield their contents of MCC upon application of aqueous fluid. This embodiment controlled a problem caused by the high hygroscopicity of Composition A, which caused it to sometimes become sticky and tacky by virtue of reaction with moisture in the air and on the surface of the carpet.

Composition B: Liquid Carpet Deodorizer

| Disodium monozinc citrate (MZC) | 20% |
| --- | --- |
| Sodium bicarbonate | 5% |
| Triton X-100 | 1% |
| Water | q.s. 100% |

This composition, utilizing zinc as the active cation, is a colorless solution, possessing no odor. As such, it can be sprayed directly on the surface of the carpet in a quantity sufficient to penetrate through the carpet itself, the underpart and to the underlying surface. The odor causing materials are neutralized, although in a slightly longer time frame than with composition A above. (2–3 minutes as opposed to 1–2 minutes.) Composition B might be preferable in home-use situations where application of the powdered material of composition A might be too onerous. Regardless, both of these compositions are highly effective in neutralizing carpet odors and meet the requirements outlined above.

EXAMPLE 3

Deodorizing Transportation Vehicles and Other Closed Environments

Passenger aircraft represent an isolated environment subject to occurrences which, if they occurred on land, would be easily remedied but, in-flight, present special difficulty. For instance, air sickness can lead to expulsion of highly odoriferous material into the upholstery, foam padding utilized in seating materials, as well as in carpeting. In the closed space of an aircraft cabin, such "spills" can present a highly objectionable odor that can adversely affect other passengers. A product is needed to quickly eliminate the odors associated with such in-flight accidents. Additionally, the product must be non-hazardous, non-flammable, nontoxic and non-corrosive to the alloys and other components of the air frame and passenger compartment. A product lacking these attributes would be dangerous and unapproved for use by agencies involved in aircraft safety. The product should have no inherent odor because strong odors in the closed environment of the aircraft cabin are considered objectionable by passengers. A composition which satisfies all of the above requirements is disclosed below, all percentages being in weight percent:

| | |
|---|---|
| Disodium monozinc citrate (MZC) | 10% |
| Fluorocarbon surfactant FSN (Dupont) | 0.5% |
| Sodium bicarbonate | 1% |
| Water | q.s. 100% |

Due to the extremely hydrophobic nature of materials generally utilized in aircrafts, such as: polyolefin fabrics, carpeting, and polyurethane foams, it was found to be extremely difficult to penetrate into fibers and crevices. That is, spillage of relatively large volumes of material in the aircraft resulted in the sequestering of small amounts of the odor-causing agents in barely-accessible spaces. While the bulk of the material could be easily cleaned up, these small, residual amounts were inaccessible. Because of the hydrophobic character of the materials involved, aqueous solutions could simply not find their ways to the odor sources. Solvent-based materials are considered hazardous in terms of flammability and usually possess obtrusive, unacceptable odors. It was found that the fluorinated surfactant, Dupont FSN, a material which lowers the contact angle of water to essentially zero, enabled the active ingredient, MZC, and the buffer, sodium bicarbonate, to migrate effectively to the source of the odor-causing agent. It was found that many surfactant materials were chemically incompatible with the MZC, resulting in destruction of the 1:1 complex. FSN was found to be effective as a surfactant as well as chemically compatible with MZC.

EXAMPLE 3

Deodorizing Self Contained Toilets

As mentioned above, the aircraft environment is very special in its requirements for safety. Aircraft toilets are self-contained units possessing holding tanks, recirculating pumping systems and a special antifreeze fluid to both cleanse the interior of the system and prevent any odor formation that could permeate the air in the cabin of the aircraft. Odor control in this unit has historically been accomplished by utilizing high concentrations of formaldehyde to kill bacteria and denature proteins. This approach has been relatively effective. However, as is well-known, formaldehyde is a gas. Even at standard pressure, at sea level, the vapor pressure of this gas is sufficient to release the gas from aqueous solution. At cruising altitudes, aircraft cabin pressure is considerably reduced below that of 760 millimeters of mercury. In this lower-pressure atmosphere, formaldehyde gas escapes from the aqueous fluid used in the aircraft toilet system at an increased rate. Entering the aircraft's ventilation system, formaldehyde gas becomes recirculated throughout the aircraft interior. On long, transcontinental or transoceanic flights, the concentration of formaldehyde in the atmosphere can reach levels sufficient to cause eye and respiratory irritation. This necessitates the rapid exchange of contaminated air for fresh, outside air. This is a costly proposition in terms of fuel. Also, in recent years, it has become increasingly well-known that formaldehyde is a potential carcinogenic agent. For this reason, its use has come into disfavor. Replacements for the odor control characteristics of formaldehyde are needed, not only in the aircraft environment, but also in other semi-closed/isolated environments. These include boats, campers, buses and trains, among others. Thus, a composition for use in eliminating odors associated with self-contained toilet must be safe, must have low toxicity and must be non-corrosive to equipment. As mentioned above, this is especially important in the case of aircraft utility. A composition which satisfies all of the above requirements is disclosed below, all percentages being in weight percent:

| | |
|---|---|
| MCC | 18% |
| Sodium carbonate | 15% |
| Sodium dodecylbenzene sulfonate | 2% |
| Dark-blue dye | 2% |
| Citrus fragrance | 1% |
| TEA sulfonate, Nasul-LB (Vanderbilt Co.) | 2% |
| Water | q.s. 100% |

This composition, when added to the holding tank fluid of the aircraft or other recirculating toilet, effectively inhibits the formation of odors. It also neutralizes extant odors. Surprisingly, this composition works extremely well at an elevated pH level of approximately 10.8. This is surprising because the 1:1 complex, MCC, exhibits nearly maximum stability at this concentration of hydrogen ions. Even so, the demand for metal ion is so great in the moiety present in the recirculating fluid that the copper ion is still available for useful reactions including, but not limited to, reactions with sulfides, nitrogen compounds such as skatoles, proteinaceous residues such as sumydryal groups and amino residues. It must be mentioned that such a high concentration of MCC, in a pure, aqueous state, is highly corrosive to aluminum, magnesium and alloys of these materials as found in the airframe of aircraft. Remarkably, this corrosive property is attenuated and even eliminated by formulating the MCC to perform useful functions. The Nasul-LB functions as a corrosion inhibitor with reference to metallic surfaces; however, it is essentially inert with respect to the 1:1 complex.

Thus, the use of this composition may potentially eliminate a severe public health hazard, namely formaldehyde exposure. It has also controlled, to a superior degree, the foul odors normally inherently present in recirculating toilets.

EXAMPLE 4

Airborne malodors

Experiments were conducted to determine the odor controlling characteristics of MCC and disodium monozinc (II) citrate (MZC). Experiments 1–3, 6, and 8 utilized MCC, while experiments 4, 5, and 7 utilized the MZC solution. The solution preparation, and experimental conditions are detailed below.

Solutions of MCC and MZC were prepared as follows: a 1.53 molar solution was diluted one hundredfold with distilled water to yield a 15.3 millimolar (mM) solution. A second solution was prepared by diluting this 15.3 mM solution 1:10 to yield a 1.53 mM solution. These solutions were placed in pump-type spray bottles capable of delivering a "fine mist."

In a room with a volume of approximately 900 cubic feet, a gaseous malodor was produced in the following way: a 0.1M solution of sodium sulfide was acidified with a 0.1M solution of citric acid yielding hydrogen sulfide ($H_2S$) which was then contained. A group of people were asked to enter the room and the $H_2S$ container was opened at a point approximately 8 feet from the group. In several seconds, all of the people said they detected the obnoxious odor of rotten eggs. The $H_2S$ generator was then closed to preclude further evolution of gas. After approximately two minutes, the group stated that they still smelled a very strong rotten egg odor.

The presence of $H_2S$ in amounts as small as 1 ppm can be easily detected by most human beings. If $H_2S$ is present at levels more than 5–10 ppm, it also can be initially detected. However, very soon, at these high level (within as little as one minute), $H_2S$ in small concentrations can no longer be detected, because it causes olfactory fatigue resulting in no odor perception. The fact that the group of people could smell the rotten eggs for several minutes indicated that the concentration of H2S was approximately in the range of 1–5 ppm.

Experiment 1

Six sprays (approx. 0.6 ml each) from the aerosol pump of the 15.3 mM solution, were introduced into the area. Within about 10 seconds, the subject group stated that they could no longer smell the rotten egg odor. At that time, another subject entered the other end of the 900 cubic foot room and stated that she still smelled the rotten egg odor. This new subject was approximately 15 feet away from the group. Two more aerosol sprays of the solution were made in the area of the new subject who then stated, almost immediately, that she could no longer detect the rotten egg smell.

Experiment 2

The procedures of Experiment 1 were repeated with a 1.53 mM solution with similar results.

Experiment 3

An artificial apple fragrance was added to the 1.53 mM solution. This formulation was tested by repeating the procedure of Experiment 1 with one person. He stated that the rotten egg odor disappeared immediately and was replaced by a pleasant fragrance which he could not identify.

Experiment 4

An experiment similar to Experiment 1 was performed using a 15.3 mM concentration solution of MZC. The odors were markedly reduced but not totally eliminated as in the case of the copper complex.

Experiment 5

An experiment similar to Experiment 1 was performed using a 1.53 mM concentration solution of MZC. Once again, the odors were markedly reduced but not totally eliminated as in the case of the copper complex. Nevertheless, there was a marked reduction in the rotten egg smell by both of the MZC solutions.

Experiment 6

In another trial, a bottle of ammonium hydroxide, 28% solution, was opened in the presence of several people who immediately complained of a choking sensation and a strong ammonia odor in the air. The 15.3 mM solution of MCC was aerosol sprayed into the area. Within 10 seconds, the subject group stated that they no longer smelled the ammonia.

Experiment 7

A repeat of the ammonia trial of Experiment 6, employing a 15.3 mM solution of MZC, did not clear the ammonia smell even after 5 minutes.

Experiment 8

The procedures of Experiment 6 were repeated once more employing a 1.53 mM solution of MCC. After 5 minutes, the employees reported no more ammonia odor. However, the results were not nearly as dramatic as when employing the 15.3 mM solution of MCC.

Clearly, both MCC and MZC can be successfully employed as odor neutralizers for airborne malodors by atomizing or aerosoling an effective amount of either substance. An effective amount appears to range from about one mM to about 16 mM concentrations into the air containing the airborne malodor. The effective amount varies somewhat for various malodors; the effective amount is different for different 1:1 complexes.

Thus, it is apparent that there has been provided a metal complex for use in controlling odors, in accordance with the present invention, which satisfies the aspects and objects as set forth above. While the invention has been described in conjunction with specific embodiments, it is evident that many alternatives, modifications and variations will be apparent to those skilled in the art in light of the foregoing description and examples, and without deviating from the contemplated scope of the present invention. Accordingly, it is intended to embrace all such alternatives, modifications and variations which fall within the spirit and scope of the appended claims.

I claim:

1. A method of reducing malodor comprising the step of:

delivering at or near the source of said malodor an effective amount of a (1:1) metal complex comprising dialkali monometal polyfunctional organic ligand chelate, and a compatible admixture wherein said admixture is a buffer, said metal complex acting as an oxidation catalyst in the presence of oxygen to chemically neutralize the source of said malodor.

2. A method of neutralizing ammonia gas comprising the steps of:

delivering at or near the source of said ammonia gas a solution containing;

an effective amount of a (1:1) metal complex comprising dialkali monometal polyfunctional organic ligand chelate, a buffer a substance to lower the freezing point of said solution, said metal complex acting as an oxidation catalyst in the presence of oxygen to chemically neutralize the ammonia gas.

3. The method of claim 2 wherein said buffer solution is triethanolamine.

4. The method of claim 1 wherein the metal complex is dialkali monocopper(II)citrate.

5. The method of claim 1 wherein the malodor source is an aqueous dispersion of a complex mixture.

6. The method of claim 1 wherein the admixture is an aqueous solution.

7. The method of claim 6 wherein the admixture contains an added surfactant.

8. The method of claim 6 wherein the admixture has a pH of about 5 to 9.

9. The method of claim 1 wherein the metal complex is dialkali monozinc(II)citrate.

10. The method of claim 1 wherein the metal complex is dialkali monomanganese(II)citrate.

11. The method of claim 2 wherein said substance to lower the freezing point is propylene glycol.

12. The method of claim 1 wherein said source of said malodor is in a carpet and said metal complex and said admixture combination is either a powder or a liquid.

13. The method of claim 1 wherein said source of said malodor is in a self-contained toilet.

\* \* \* \* \*